United States Patent [19]

Geen et al.

[11] Patent Number: 5,684,153
[45] Date of Patent: Nov. 4, 1997

[54] PROCESS FOR THE PREPARATION OF PURINE DERIVATIVES

[75] Inventors: Graham Richard Geen, Stansted Mountfitchet; Richard Lewis Jarvest, Surbiton, both of England

[73] Assignee: Beecham Group plc, Brentford, United Kingdom

[21] Appl. No.: 258,167

[22] Filed: Jun. 10, 1994

Related U.S. Application Data

[63] Continuation-in-part of Ser. No. 132,082, Oct. 5, 1993, abandoned, and Ser. No. 918,111, Jul. 20, 1992, abandoned, which is a continuation of Ser. No. 607,403, Oct. 31, 1990, abandoned, which is a division of Ser. No. 85,216, Aug. 12, 1987, Pat. No. 5,075,445, which is a continuation of Ser. No. 641,300, Aug. 16, 1984, abandoned, said Ser. No. 132,082, is a continuation of Ser. No. 825,440, Jan. 22, 1992, Pat. No. 5,250,688, which is a continuation of Ser. No. 285,399, Dec. 15, 1988, abandoned, which is a continuation of Ser. No. 777,188, Sep. 18, 1985, abandoned.

[51] Int. Cl.[6] .................. C07D 473/18; C07D 473/32
[52] U.S. Cl. ............................. 544/276; 544/277
[58] Field of Search ........................ 540/277, 276

[56] References Cited

U.S. PATENT DOCUMENTS 5,075,445  12/1991  Jarvest et al. ........................ 544/276
5,246,937   9/1993  Harnden et al. ...................... 514/261

FOREIGN PATENT DOCUMENTS 0 055 23  12/1981  European Pat. Off. ...... C07D 473/18

OTHER PUBLICATIONS

Geen et al., *Tetrahedron*, 46:19, 6903–6914, (1990).

Chu et al., *J. Heterocyclic Chem.*, 23, 289 (1986).

Robins et al., *Can. J. Chem.*, 60 (1982).

Kjellberg et al., *Nucleosides & Nucleotides*, 8:2, 225–256 (1989).

*Primary Examiner*—Mark L. Berch
*Attorney, Agent, or Firm*—Dara L. Dinner; Stephen Venetianer; Edward T. Lentz

[57] ABSTRACT

The present invention provides a process for the synthesis of penciclovir and famciclovir by 9-substituting the compound 2-amino-6-chloropurine (ACP) with 2-acetoxymethyl-4-(leaving group)-but-1-yl acetate, followed by displacement of the 6-chloro moiety with a hydroxy moiety (i.e. to form a guanine derivative) or with hydrogen (to form the 2-aminopurine derivative), respectively.

5 Claims, No Drawings

PROCESS FOR THE PREPARATION OF PURINE DERIVATIVES

This is a continuation-in-part application of U.S. Ser. No. 08/132,082, filed 5th Oct. 1993, now abandoned, which is a continuation of U.S. Ser. No. 07/825,440, filed Jan. 22, 1992, now U.S. Pat. No. 5,250,688, which is a continuation of U.S. Ser. No. 07/285,399 filed 15 Dec. 1988, now abandoned which is a continuation of U.S. Ser. No. 06/777, 188, filed Sep. 18, 1985, now abandoned; and U.S. Ser. No. 07/918,111 filed 20th Jul. 1992, now abandoned, which is a continuation of U.S. Ser. No. 07/607,403 filed 31 Oct. 1990, now abandoned, which is a division of U.S. Ser. No. 07/085,216 filed 12 Aug. 1987, now U.S. Pat. No. 5,075, 445, which is continuation of U.S. Ser. No. 06/641,300 filed 16 Aug. 1984 now ABN.

The present invention relates to a process for the preparation of novel compounds which are of potential use as antiviral agents, to a process for their preparation and to their use as pharmaceuticals.

U.S. Pat. Nos. 5,075,445 and 5,246,937, the subject matter of which is incorporated herein by reference, disclose antiviral compounds penciclovir (Example 4 of '445) and famciclovir (Example 2 of '937) and methods for their preparation. 2-Amino-6-chloropurine (ACP) is 9-substituted with an appropriate side chain precursor, followed by conversion of the 6-chloro moiety to a hydroxy moiety (i.e. to form a guanine) or hydrogen (a 2-aminopurine).

In particular, beginning column 4 of '445, and column 3 of '937, a process is described for the preparation of such purine derivatives wherein the hydroxy groups in the 9-(4-hydroxy-3-hydroxymethylbut-1-yl) substituent are in acylated form, i.e. the ACP is reacted with 2-acyloxymethyl-4-(leaving group)-but-1-yl acylate. The leaving group may be halo, such as chloro, bromo or iodo although alternative leaving groups, such as tosylate or methanesulphonate may be employed. The acyl groups have advantages over the alternative protecting groups already described in acyclonucleoside chemistry in providing a good yield of 9-substitution and avoiding by-products which are difficult to isolate.

The following examples illustrate the process of the invention to form 9-(4-acetoxy-3-acetoxymethylbut-1-yl)-2-amino-6-chloropurine, (DACP). The following descriptions illustrate the preparation of side chain intermediates. Penciclovir is prepared from DACP according to the method described in '445 column 14, lines 4–16 and famciclovir is prepared from DACP according to the method described in Example 2 of '937.

EXAMPLE 1

2-Acetoxymethyl-4-bromobutyl acetate was reacted with ACP as described in Examples 11 and 10 of '445.

EXAMPLE 2

A mixture of ACP (10.0 mmol), 2-acetoxymethyl-4-iodobutyl acetate (3.30 g, 10.5 mmol), and anhydrous potassium carbonate (2.07 g, 15.0 mmol) was stirred for 18 hours at ambient temperature in dry DMF (40 ml) under an atmosphere of dry nitrogen. The mixture was then filtered to remove insoluble material, which was washed well with DMF. The combined filtrates were evaporated under reduced pressure and the residue purified directly by column chromatography on silica gel (150 g), eluting with various dichloromethane—methanol mixtures. Fractions containing the first-eluting N-9 isomer, and the second-eluting N-7 isomer were separately combined, rigorously evaporated and weighed. The N-9:N-7 alkylated product ratio obtained from the isolated weights was checked by integration of the respective H-8 $^1$HNMR signals in the spectrum of the crude residue.

9-(4-Acetoxy-3-acetoxymethylbutyl)-2-amino-6-chloropurine and 7-(4-acetoxy-3-acetoxymethylbutyl)-2-amino-6-chloropurine Column eluant dichloromethane-methanol 25:1.

9-isomer, 75%, m.p. 134°–136° (ethyl acetate-diethyl ether).

$^1$HNMR: 1.80–2.05 (m 3H,CHCH$_2$), 2.00 (s,6H,2× COCH$_3$), 4.03 (d,4H,2×CH$_2$O), 4.15 (t,2H,CH$_2$N), 6.87 (brs,2H,NH$_2$), 8.16 (s,1H,H-8). $^{13}$CNMR: 20.47 (2×CH$_3$), 27.75 (CH$_2$), 34.45 (CH), 40.88 (CH$_2$N), 63.43 (2×CH$_2$O), 123.43 (C-5), 143.07 (C-8), 149.34 (C-6), 154.02 (C-4), 159.68 (C-2), 170.27 (2×CO).

U.V. $\lambda_{max}$ 223.5 ($\epsilon$27.600), 248.5 (5,800), 310 (7,700). Found; C:47.14, H:4.97, N:19.69. C$_{14}$H$_{18}$N$_5$O$_4$Cl requires; C: 47.26, H:5.10, N:19.68%.

7-isomer, 15%, m.p. 159°–161° (dec). (butanol).

$^1$HNMR: 1.60–2.10 (m,3H,CHCH$_2$), 2.00 (s,6H,2× COCH$_3$), 4.00 (d,4H,2×CH$_2$O), 4.34 (m,2H,CH$_2$N), 6.56 (brs,2H,NH$_2$), 8.33 (s,1H,H-8). $^{13}$CNMR:20.41 (2×CH$_3$), 29.80 (CH$_2$), 34.51 (CH), 44.06 (CH$_2$N), 63.46 (2×CH$_2$O), 114.65 (C-5), 141.97 (C-6), 149.28 (C-8), 159.81 (C-2), 164.24 (C-4), 170.12 (2×CO).

U.V. $\lambda_{max}$ 222.5 ($\epsilon$23.600), 253.5sh (3,700), 323 (5,400) Found; C:47.31, H:5.17, N: 19.88. C$_{14}$H$_{18}$N$_5$O$_4$Cl requires; C:47.26, H:5.10, N:19.68%.

2-Acetoxymethyl-4-bromobutyl acetate was prepared as described in Examples 5–8 of '445

2-Acetoxymethyl-4-iodobutyl acetate was prepared as follows a) To a stirred solution of 2-(2-benzyloxyethyl)propane-1, 3-diol (J. Org. Chem., 1981, 46, 3204) (10.0 g, 47.6 mmol), 4-dimethylaminopyridine (0.55 g, 4.5 mmol), and pyridine (12.3 ml, 0.15 mol) in dichloromethane (54 ml) at −10° C. was added dropwise acetic anhydride (13.2 ml, 0.14 mol) over 20 minutes. After completion of the addition, the reaction mixture was stirred for a further 1 hour at 0° C., then diluted with dichloromethane (100 ml) and washed with 2M hydrochloric acid (2×50 ml), saturated sodium bicarbonate solution (50 ml), and brine (50 ml), dried (MgSO$_4$), and evaporated to give 2-acetoxymethyl-4-benzyloxybutyl acetate as a light yellow oil (13.2 g, 94%). b.p. 160°–165°/0.5 mm.

$^1$HNMR: 1.62 (q,2H,CHCH$_2$), 2.00 (s,6H,2×CH$_3$), 2.15 (m,1H,CH), 3.51 (t,2H,CH$_2$CH$_2$O), 4.03 (m,4H,2×CH$_2$O), 4.46 (s,2H,OCH$_2$Ph), 7.33 (m,5H,Ph).

$^{13}$CNMR: 20.31 (2×CH$_3$), 27.93 (CHCH$_2$), 34.40 (CH), 63.73 (2×CH$_2$O), 67.22 (CH$_2$CH$_2$O), 71.99 (CH$_2$Ph), 127.22, 127.30, 128.09, 138.54 (Ph), 170.13 (2×CO). Found; C:65.07, H:7.76. C16H22O$_5$ requires; C:65.29, H:7.53%.

b) A solution of 2-acetoxymethyl-4-benzyloxybutyl acetate (15.5 g, 52.7 mmol) in ethanol (200 ml) was hydrogenated for 18 hours at ambient temperature over 10% palladium-carbon (2 g). Filtration and evaporation afforded the corresponding alcohol (10.2 g) as a colourless oil.

c) To a stirred solution of the above oil and triethylamine (10.4 ml, 74.8 mmol) in dichloromethane (100 ml) cooled to −5° C. was added a solution of methanesulphonyl chloride (4.6 ml, 59.5 mmol) in dichloromethane (30 ml) dropwise over 30 minutes. After completion of the addition, the reaction mixture was stirred for a further 1 hour at −5° C., then washed with 2M hydrochloric acid (2×100 ml), saturated sodium bicarbonate solution (100 ml), and brine (100 ml), dried (MgSO$_4$) and evaporated to afford the corresponding methanesulphonate (14.1 g) as a pale yellow oil.

d) A mixture of the above oil and sodium iodide (15.0 g, 0.1 mol) was stirred under reflux for 2 hours in acetone (150 ml), then cooled, poured into water (300 ml), and extracted with diethyl ether (3×150 ml). The combined ether extracts were washed with 10% sodium metabisulphite solution (250 ml), and brine (250 ml), dried (MgSO$_4$) and evaporated to give a pale oil. This was purified by flash column chromatography on silica, eluant hexane-diethyl ether 3:2 affording the title compound as a colourless oil (13.1 g, 79% from 2-acetoxymethyl-4-benzyloxybutyl acetate).

$^1$HNMR: 1.88 (q,2H,CH$_2$), 2.02 (s,6H,2×CH$_3$), 2.10 (m,1H,CH), 3.33 (t,2H,CH$_2$I), 4.02 (d,4H,2×CH$_2$O).

$^{13}$CNMR: 5.01 (CH$_2$I), 20.48 (2×CH$_3$), 32.04 (CH$_2$), 37.87 (CH), 62.86 (2×CH$_2$O), 170.02 (2×CO).

EI-MS. m/e: 314 (M$^+$), 254 (M$^+$-HOAc), 211 (M$^+$-HOAcAc), 187 (M$^+$-I). Found; C:34.56, H:4.99. C$_9$H$_{15}$O$_4$I requires; C:34.42, H:4.81%.

We claim:

1. A process for the preparation of i) penciclovir or ii) famciclovir which process comprises the reaction of 2-amino-6-chloropurine with 2-acetoxymethyl-4-(leaving group)-but-1-yl acetate;

to give 9-(4-acetoxy-3-acetoxymethylbut-1-yl)-2-amino-6-chloropurine;

and thereafter:

i) hydrolysing to give penciclovir:

or ii) reducing to give famciclovir.

2. A process according to claim 1 wherein the leaving group is halo.

3. A process according to claim 2 wherein the halogen is chlorine.

4. A process according to claim 2 wherein the halogen is bromine.

5. A process according to claim 2 wherein the halogen is iodine.

* * * * *